United States Patent [19]

Kopunek et al.

[11] Patent Number: 4,776,704
[45] Date of Patent: Oct. 11, 1988

[54] MIXING AND DISPENSING SYRINGE

[75] Inventors: Thomas V. Kopunek, Lewes; Richard E. Welsh, Milford; Paul D. Hammesfahr, Dover, all of Del.

[73] Assignee: Dentsply Research & Development Corp., Milford, Del.

[21] Appl. No.: 941,471

[22] Filed: Dec. 15, 1986

[51] Int. Cl.[4] .......................... B01F 15/02; B01F 5/06
[52] U.S. Cl. .................................... 366/184; 222/145; 222/386; 366/339; 366/332; 604/89
[58] Field of Search ............... 366/184, 189, 190, 336, 366/338, 339, 340, 267, 332, 333, 334, 335; 222/190, 145, 386; 604/56, 82, 89, 92, 416

[56] References Cited

U.S. PATENT DOCUMENTS

| | | |
|---|---|---|
| 1,100,799 | 6/1914 | Wedig . |
| 2,698,015 | 7/1951 | Brown . |
| 3,016,896 | 1/1962 | Sickle . |
| 3,076,456 | 2/1963 | Hunt . |
| 3,164,303 | 1/1965 | Trautmann . |
| 3,195,778 | 7/1965 | Coates . |
| 3,286,992 | 11/1966 | Armeniades et al. . |
| 3,437,242 | 4/1969 | Poitras . |
| 3,475,010 | 10/1969 | Cook .................................. 366/333 |
| 3,477,431 | 11/1969 | Walecka . |
| 3,563,415 | 2/1971 | Ogle . |
| 3,593,964 | 7/1971 | Morane . |
| 3,606,094 | 9/1971 | Mills et al. . |
| 3,635,444 | 1/1972 | Potter . |
| 3,664,638 | 5/1972 | Grout et al. . |
| 3,699,961 | 10/1972 | Szpur . |
| 3,735,900 | 5/1973 | Gores . |
| 3,889,674 | 6/1975 | Cilento . |
| 4,014,463 | 3/1977 | Hermann . |
| 4,050,676 | 9/1977 | Morishima et al. . |
| 4,207,009 | 6/1980 | Glocker . |
| 4,208,133 | 6/1980 | Korte-Jungermann . |
| 4,479,578 | 10/1984 | Brignola et al. . |
| 4,522,504 | 6/1985 | Greverath . |
| 4,538,920 | 9/1985 | Drake . |

Primary Examiner—Robert W. Jenkins
Attorney, Agent, or Firm—David E. Wheeler; Edward J. Hanson, Jr.

[57] ABSTRACT

A mixing and dispensing syringe having a single mixing cylinder loadable at one end with a plurality of different materials to be blended and mixed by static devices, a dispensing nozzle on the opposite end of said cylinder, a piston-like unit axially movable in the cylinder between opposite ends thereof by means of a manually-operable member connected to one end of the unit, whereby, when the unit is positioned nearest the nozzle in the cylinder and the cylinder is loaded with the materials to be mixed, movement of the unit toward the loadable end of the cylinder causes the materials to pass through a mixing device in the unit and into a common chamber or barrel of the syringe to effect partial mixing and when the unit next is moved toward the nozzle by the manual member, the partially mixed materials then pass through the static mixing device in the nozzle and are further mixed incident to being discharged from the syringe.

14 Claims, 1 Drawing Sheet

U.S. Patent    Oct. 11, 1988    4,776,704
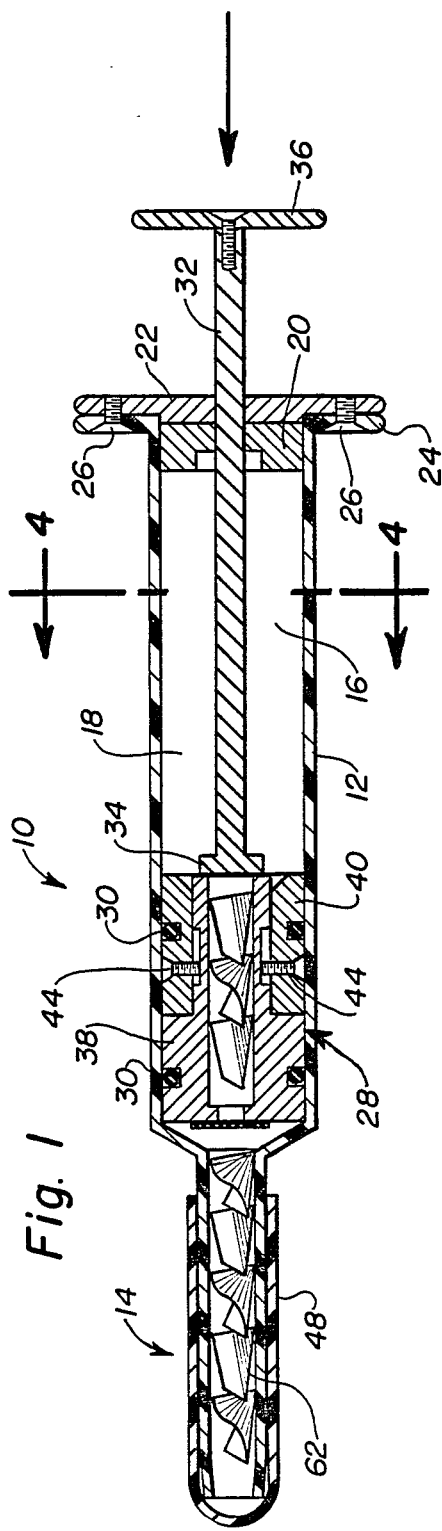
Fig. 1
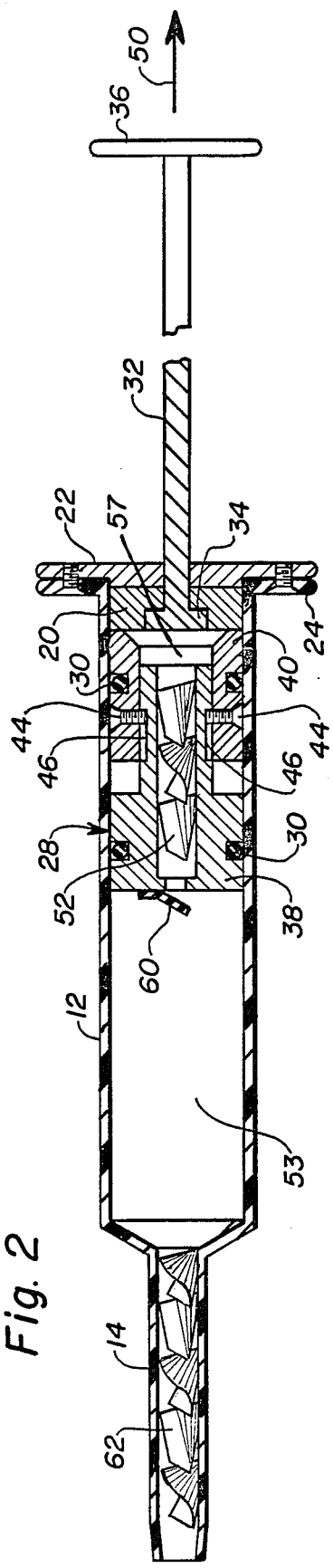
Fig. 2
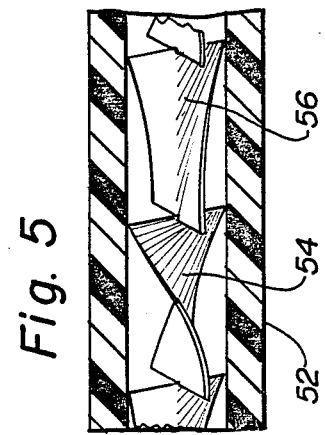
Fig. 4
Fig. 5
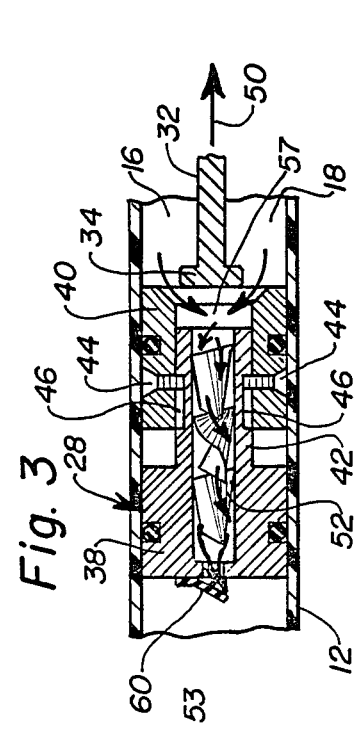
Fig. 3

MIXING AND DISPENSING SYRINGE

BACKGROUND OF THE INVENTION

In the practice of dentistry, as well as in some aspects of medical practice, it is necessary to mix certain components to produce a mixed product useful for various purposes. Certain types of cement and filling materials fall in this category and, the production of a viscous mix of several ingredients to form impression material in the practice of dentistry for the production of various types of artificial dental appliances and the like is another category in which mixed materials are employed. For many years, materials of this type were mixed in mixing containers manually and, more recently, devices have been developed capable of accepting the necessary ingredients for a certain product and mixing, as well as dispensing the same from a device in which so-called static mixing units or mechanisms accomplish the mixing of the ingredients incident to being discharged from a nozzle, for example.

Examples of such static mixing devices as have been developed previously are represented in certain prior U.S. Patents of which the following are outstanding examples thereof:

U.S. Pat. No. 3,286,992—Armeniades et al—Nov. 22, 1966
U.S. Pat. No. 3,862,022—Hermann—Jan. 21, 1975
U.S. Pat. No. 3,923,288—King—Dec. 2, 1975
U.S. Pat. No. 4,183,682—Lieffers—Jan. 15, 1980
U.S. Pat. No. 4,207,009—Glocker—June 10, 1980
U.S. Pat. No. 4,538,920—Drake—Sept. 3, 1985

In the main, the foregoing patents are directed to the details of the static mixing units and supposedly comprise improvements in the capabilities of the mixing elements facilitating the intermixing of two or more ingredients. All of them have only a single elongated mixing unit through which the material passes once and then is considered to be mixed. Few of them show the source of the materials which are introduced into the static mixing units, with the exception of U.S. Pat. No. 4,538,920, in which it is seen that a pair of cylindrical containers are mounted in side-by-side relationship and the outlets merge into a common static mixing unit, the cylinders employing plunger members to effect discharge from the cylinders into the mixing unit.

It is the primary object of the present invention to improve the mixing of at least two ingredients more thoroughly than contemplated by the prior art and in a very simplified manner, details of the structure which accomplishes this being set forth below:

SUMMARY OF THE INVENTION

It is the principal object of the present invention to provide a mixing and dispensing syringe employing a single cylinder having a loading opening at one end and a dispensing nozzle at the opposite end, the cylinder containing a piston-like unit axially movable within the cylinder between opposite ends and a static mixing device is included in said unit, and a second static mixing device is also included in the discharge nozzle affixed to the cylinder, whereby, when the piston-like unit is in the end of the cylinder nearest the nozzle, preferably plural compartments are provided in the cylinder respectively for the introduction of different ingredients and the filling end of the cylinder then is closed, followed by manually moving the piston-like unit toward the filling end of the cylinder and incidentally forcing the ingredients through the static mixing device in the piston-like unit to effect a partial mixing thereof, and at the end of such mixing stroke, reverse movement of the piston-like unit is effected by means of a manually-operated member connected thereto which causes the piston-like unit to function solely as a piston while being moved toward the discharge nozzle and thereby force the partially mixed material through the static mixing device in the discharge nozzle to effect complete mixing thereof as a finished product capable of being discharged forthwith into an impression tray or directly about the teeth in the event the mixed ingredients are for purposes of making a dental impression. Obviously, various other mixed materials may be used for other purposes.

It is another object of the invention to provide an elongated manual-operating member connected to one end of the piston-like unit for purposes of moving the same in opposite directions within the cylinder, said operating member being of a flat nature and extending diametrically and longitudinally within the cylinder and slidably engaging opposite portions of the inner walls of the cylinder to form the aforementioned plurality of compartments in which different ingredients respectively are filled prior to mixing the same.

One further object of the invention is to provide on the end of the piston-like unit nearest the nozzle, a one-way valve capable of permitting material which is mixed by the static mixing device in the piston-like unit during movement of the latter toward the filling end of the cylinder but said valve being closed immediately upon opposite movement of the piston-like unit toward the nozzle, whereby the piston-like unit then functions solely as a piston to force the partially mixed material through the static mixing device in the nozzle and effect a substantially complete mixture of the ingredients, depending upon the length and extent of the several static mixing devices of the nature described above.

Still another object of the invention is to form the respective static mixing devices in the nature of an elongated string of mixing elements respectively capable of reversing or otherwise agitating the ingredients as being mixed, and in the preferred embodiment of the invention, a greater number and thereby, a longer string of said members are employed in the nozzle than in the static mixing device in the piston-like unit.

One still further object of the invention is to provide a suitable cap member to enclose the nozzle and otherwise load the compartments of the cylinder with the materials to be mixed and preferably hermetically seal the entire syringe in condition for use at any desired time and, preferably manufacture the various components, with the possible exception of the members of the static mixing device, from suitable relatively rigid plastic material formed by injection molding and thereby adapt the same to relatively inexpensive production, whereby at the completion of a discharge of mixed material from the syringe, it may be discarded. Details of the foregoing object of the invention, as well as other objects thereof, are set forth in the following specification and illustrated in the accompanying drawing comprising a part thereof.

BRIEF DESCRIPTION OF THE DRAWING

FIG. 1 is a longitudinal sectional view of a syringe embodying the principals of the present invention and illustrating the piston-like unit in the initial starting position, and also showing two cavities for respectively receiving different materials to be intermixed.

FIG. 2 is a view similar to FIG. 1 but showing the piston-like unit in retracted position from that shown in FIG. 1, and thereby showing partially mixed material in the fore part of the chamber of the syringe in position for the piston-like unit to be projected forwardly toward the nozzle and thereby force the partially mixed material through the stationary mixing device in the nozzle and thereby subject it to final mixing.

FIG. 3 is a fragmentary longitudinal sectional view showing the piston-like unit as it appears during its movement from the position shown in FIG. 1 to that shown in FIG. 2.

FIG. 4 is a transverse sectional view taken on the line of 4—4 of FIG. 1.

FIG. 5 is a partial longitudinally sectional view on a larger scale than employed in the preceding figures and showing details of the mixing members in one of the static mixing devices of the invention.

DETAILED DESCRIPTION OF THE PREFERRED EMBODIMENT OF THE INVENTION

The syringe 10 comprises a body in the form of a cylinder 12 of uniform transverse diameter and having mounted on one end a discharge nozzle 14 and the other end of the cylinder adapted to be opened to permit several components respectively to be mounted within chambers 16 and 18, provided to receive the respective materials which are to be intermixed by the syringe. The filling opening at said opposite end of the cylinder 12 is closed by a seal plunger 20 and a closure 22 abuts a flange 24 and is adapted to be removably secured thereto by means of a pair of headed members 26 affixed to the closure 22 and operable within bayonet-type slots, not shown, in flange 24. A snap fit closure can be used in some instances to secure the closure 22 in closed position.

Slidably mounted within the cylinder 12 is a piston-like unit 28, which is slidable longitudinally within the cylinder in close relationship to the walls thereto and to effect a close sealing operation. A pair of O-rings 30 are formed in the circumference of the unit 28 for slidable engagement with the inner walls of cylinder 12. In some preferred constructions the O-rings are unnecessary.

One end of an elongated manual-operating member 32 is connected by a head 34 to one end of the body of the unit 28, as clearly shown in FIGS. 1–3, and said member extends through appropriate openings in the seal plunger 20 and closure 22 for close fitting slidable movement. An operating button 36 is affixed to the outermost end of the member 32 to facilitate manual operation thereof.

Referring to FIGS. 1–3, especially FIG. 3, it will be seen that the unit 28 comprises a pair of members which are longitudinally slidable with respect to each other to a limited extent. Said unit comprises a forward member 38 and a rearward member 40. The forward member 38 has a male portion 42 thereon slidably movable a limited distance within a complementary bore in the rearward member 40, as clearly shown in FIGS. 1–3. Restricted movement is effected by a pair of screws 44 in the rearward member 40 operable within grooves or slots in the male portion 42. The restricted movement can be provided by a lug and slot arrangement in which assembly is obtained initially by fitting together and twisting to align the lug with the slot.

In operating the syringe, a piston-like unit 28 is pushed inwardly to the forward end of the cylinder 12, as shown in FIG. 1. Closure 22 then is removed by rotating the same about its axis sufficiently to disengage the screws 26 from the bayonet slots, not shown. Then the closure is pulled away from the cylinder 12 and seal plunger 20 is removed. Referring to FIG. 4, it will be seen that the elongated manual-operating member 32 is an alongated flat member extending between opposite sidewalls of the cylinder 12 and thereby defining the pair of similar chambers 16 and 18 in which respectively different materials are filled to the extent desired and adapted to be intermixed by the syringe in the manner described below. After the respectively different materials have been loaded into the chambers 16 and 18, plunger 20 is restored to its operative position in the filling end of the cylinder, as illustrated in FIGS. 1 and 2 and closure member 22 is restored to closed position and locked with respect to flange 24. In the preferred arrangement for storage and sale of the syringe, it is loaded and distributed in such manner. Preferably, the discharge nozzle 14 is covered by a suitable thimble closure 48 to maintain it in aseptic condiiton, and if desired, the entire syringe may be enclosed in suitable platic sheeting and sealed. When the components of materials are to be intermixed by the syringe, any wrappings or other enclosing means, including thimble closure 48, are removed and operating button 36 on operating member 32 is pulled outwardly in the direction of the arrow 50, shown in FIG. 2.

Referring to FIG. 3, initial movement of the operating member in the direction of the arrow 50 closes the rearward member 40 of piston-like unit 28 to be moved in a manner to extend it from the forward member 38 and separates the forward and rearward members 38 and 40 a limited extent, illustrated in FIGS. 2 and 3. This operation also moves valve head 34 of the inner end of the member 32 away from the right-hand end of the longitudinal opening in piston-like unit 28, which contains the first of a pair of static mixing devices 52 which comprises a series of preferably interconnected members, individually illustrated in FIGS. 1–3, and shown in greater detail in FIG. 5. Such movement as described effects a passage or space 57 through which the materials to be mixed can pass respectively from the chambers 16 and 18 and the same are then caused to be intermixed, at least to a partial extent by engagement with the members comprising the first static mixing device 52. When the first static mixing device 52 has been moved to the fullest extent in pre-mixing direction, as shown in FIG. 2, head 34 abuts the seal plunger 20 and movement stops. Such operation disposes all of the partially mixed material in the pre-mixing chamber 53, shown in FIG. 2.

The exact design of the static mixing device 52 may be of any of a number of different types, but for purposes of illustration in the present application, attention is directed to FIG. 5 in which it will be seen that the successive members 54 and 56 are of different types, such as, for example, member 54 may be convex while member 56 is concave and so on throughout the entire string of connected elements, it being understood that in the preferred construction, the elements are respectively connected end-to-end and agitate and disturb and materials being mixed in such manner that relatively thorough mixing hereof occurs. The essence of the present invention therefore does not lie in the specific type of mixing elements comprising the static mixing device but, as illustrated in FIG. 5, the elements of said device may be same as, or similar to, the corresponding elements shown in expired prior U.S. Pat. No. 3,286,992 to Armeniades et al, dated Nov. 22, 1966.

After the partially mixed materials have been dispoed in the pre-mixing chamber 53, it is time for the piston-like unit 28 to be moved toward the nozzle 14, in the direction of the arrow 58, shown in FIG. 1, and when this occurs, there is a check valve 60 on the forward face of the forward member 38 of the unit 28 which, if desired, may be simply in the form of a so-called flap-valve of a flexible nature, which readily operates to permit the passage of partially mixed material through the first static mixing device 52 into the pre-mixing chamber 53 but, upon reverse movement of the unit 28, valve 60 is closed and the unit 28 thereafter functions solely as a piston and pushes the partially mixed material from the pre-mixing chamber 53 through the second static mixing device 62 which, preferably, contains a somewhat larger number of successive members which effect the mixing. Specifically, solely by way of illustration, it may be that the first device 52 may contain five successive mixing members 56, while the second static mixing device 62 contains six of such successive members, but this is offered solely as an example and is not restrictive.

As an alternate to the check valve 60, it will be seen from the figure that when the manual-operating member is moved toward the nozzle, the valve head 34 is moved into abutment with the rearward end of the bore in member 40 of the unit 28 and thus closes the passage to the static mixing device in the bore in member 38, whereby, there is no need to provide check valve 60.

As the unit 28 is moved progressively toward the nozzle 14, the partially mixed materials pass through the second static mixing device 62 and therein are additionally intermixed to produce a final mixed consistency of the materials satisfactory for the intended use, such as that of being injected into an impression tray, not shown. It is obvious that the convenience of such an arrangement is advantageous and simply by so-called push-pull operation of the piston-like unit 28, successive mixing of the components of the final mixture are effected in a manner not illustrated in the prior art and the advantage of which should be apparent.

In broader aspects, the present invention can be applied to a mixing reservoir which would be represented by the cylinder 12 which is a tubular member with side wall surface substantially aligned with the path of reciprocal movement of the piston-like unit 28. The piston-like unit 28 is complimentary with the inside cross section of the tubular reservoir barrel or container 28 which initially encloses a plurality (two or more) materials in two material holding compartments, chambers 16 and 18. The piston-like unit reciprocates and on a first stroke of the reciprocal movement moves away from its position adjacent the outlet 14 to its position remote from the outlet which is at the filling end closure 22 as previously described to cause the materials to pass through the mixing device and be mixed. On the second stroke or reverse movement of the reciprocal movement, the piston-like unit moves to its position adjacent the outlet, expressing the mixed materials. The outlet 41 can be equiped with a tip that will fit on by friction or be provided with a positive coupling securement. This tip can provide for a smaller orifice or to provide a curved nozzle or the like.

A static mixer is a mixer that is stationary with regard to its mixing function, but as used in this application, in the piston-like unit, moves with respect to the material linearly and has the material thereby mixed as the piston-like member moves and the blades that it carries roll and cut the materials repetitiously to bring about mixing as the materials pass through the piston-like member. The preferred static mixer is made up of a plurality of axially-aligned blade members having reversing concave and convex surfaces as may be seen in FIG. 5.

It will be understood from the foregoing that the present invention provides a mixing syringe that provides a great deal of mixing between even very viscous and therefore hard to mix materials without requiring mechanical assist from such expedients as a lever. The aportionment of the mixing blades or stators into two different mixing units, one in the piston-like unit and the other in the outlet provides this reduction in static mixing resistance.

The foregoing description illustrates preferred embodiments of the invention. However, concepts employed may, based upon such description, be employed in other embodiments withoud departing from the scope of the invention. Accordingly, the following claims are intended to protect the invention broadly, as well as in the specific forms shown herein.

What is claimed is:

1. A mixing and dispensing syringe for viscous material comprising in combination, a single mixing cylinder having a discharge nozzle on one end and a filling entrance on the opposite end, closure means operable upon said opposite end to enclose a plurality of materials when loaded into said cylinder, a piston-like unit complementary in size with the diameter of said cylinder and movable longitudinally therein between opposite ends of said cylinder and initially positioned adjacent said nozzle, a first static mixing device in said piston-like unit and a second static mixing device in said nozzle, and an elongated manual-operating member connected at one end to said piston-like unit and extending longitudinally and slidably through said closure and adapted to be pulled outwardly relative to said closure to cause the plurality of materials to be passed through said first static mixing device to be mixed as said piston-like unit is pulled toward said closure means and, upon reversely pushing said piston-like member toward said nozzle, the partially mixed materials will be expressed through the second static mixing device in said nozzle, thereby to complete the mixing of said materials as being discharged from said cylinder, wherein each static mixing device comprises a plurality of axially-aligned members and the mixing device in said nozzle having a greater number of said members than the number in said piston-like unit, whereby a greater amount of mixing of the materials occurs in the nozzle than in the piston-like unit prior to discharge from the syringe.

2. The syringe according to claim 1, further characterized by said elongated manual-operating member comprising a flat blade-like member extending between opposite walls of said cylinder and slidably engaging the same to form a pair of material-receiving compartments when said piston-lke unit is positioned in spaced relation to the filling end of said cylinder.

3. The syringe according to claim 1, further including a one-way valve on the end of the first static mixing device in said piston-like unit nearest the nozzle, whereby, when the materials have been partially mixed by movement of the piston-like unit toward the filling end of the cylinder while the materials pass through and are mixed by dispensing into a common chamber of said syringe by passing through said first static mixing device and the piston-like unit is moved toward said optional nozzle, said valve is closed by engaging the partially mixed materials and remains closed while said partially mixed materials are passing through the static mixing device in said nozzle.

4. The syringe according to claim 1, further including an enclosing cover for said nozzle to maintain the same uncontaminated and said components of the entire syringe being composed of relatively rigid plastic material to render the same inexpensive to manufacture and permit disposal of the same and any material therein to prevent re-use.

5. The syringe according to claim 1, further characterized by piston-like unit being composed of two parts connected for limited longitudinal movement, one of said members being connected to the inner end of said operating member and the other part of said piston-like member having a sleeve-like male portion slidably received in a bore in said one of said parts, said sleeve-like male portion having a bore longitudinally therethrough which contains said first static mixing device for passage of the materials therethrough to be mixed, said connection of said one part to said operating member having a passage therethrough for movement of material to one end of said first static mixing device when said piston-like member is being moved toward said filling end of said cylinder and said other part of said piston-like member being movable to close passage to said first static mixing device when said member is moved toward the nozzle on said cylinder.

6. The syringe according to claim 5, in which movement between the parts of said piston-like member is controlled by slots of limited length being formed in one of said members and screw-like members being fixed to said other member and having portions slidable in said slots, whereby limited movement is restricted to the length of said slots.

7. A mixing reservoir comprising in combination, a reservoir member to enclose a plurality of materials, a piston-like unit comprising a mixing device means complementary with said reservoir member and reciprocally movable therein between two positions, said mixing means being a static mixing device and an outlet in said reservoir member, said mixing reservoir comprising a manual-operating member connected to said piston-like unit and extending through said mixing reservoir and dividing said mixing reservoir into at least two material-containing compartments when said piston-like unit is positioned adjacent said outlet and adapted to be moved away from said outlet on the first said stroke to cause the plurality of materials to be passed through said mixing device to be mixed, and, upon reversely moving on the second said stroke moving said piston-like member toward said outlet to express said mixed materials therefrom, wherein said mixing device means comprises a valve means adapted to be opened to pass said plurality of materials through said mixing device of said piston-like unit on a first stroke of reciprocal movement to effect at least partial mixing of said plurality of materials and closed on another stroke of said reciprocal movement when expressing said mixed materials from said outlet, wherein said reservoir is tubular with the wall surface defining said tube being substantially aligned with the path of reciprocal movement of said piston-like unit, said outlet being at one end of said tubular reservoir, said piston-like unit being complementary with the inside cross section of said tubular reservoir and movable therein between opposite ends of said tubular reservoir and initially positioned adjacent said outlet, and said piston-like unit being adapted to be moved to cause said plurality of materials to be passed through said mixing device with a rolling and cutting action mixing the plurality of materials together as said piston-like unit is moved on at least one stroke of said reciprocal movement.

8. The mixing reservoir of claim 7, further characterized by said static mixing device only partially mixing said plurality of materials, and said outlet containing a second static mixer through which mixed material is passed to effect further mixing thereof.

9. The mixing reservoir of claim 8, wherein said first and said second static mixers each comprise a plurality of axially-aligned blade members that have reversing concave and convex surfaces, the static mixing device in said outlet having a greater number of said blade members than the number in said piston-like unit, whereby a greater amount of mixing of the materials occurs while passing through the outlet than while passing through the mixing device in said piston-like unit prior to discharge from the outlet.

10. The mixing reservoir of claim 8, further including a one-way valve on the end of the first static mixing device at the end of said piston-like unit farthest from said outlet and having a valve seat on said piston-like unit and a valve member on said manual-operating member, said valve member being lifted from said seat on operation of said manual-operating member on the first stroke during which the materials are partially mixed by movement of the piston-like unit away from said outlet to cause the materials to pass through and be partially mixed by the static mixing device and when the piston-like unit is moved toward said outlet, said valve member engages said seat to close said valve when the manually-operating unit is moved toward said outlet to push said piston-like unit against the partially mixed materials and said valve remains closed while said partially mixed materials are passing through said second static mixing device in said outlet.

11. A flow control valve for a mixing and dispensing syringe comprising a piston-like unit having two longitudinally movable members having a common axis, one of said members having a bore, a static mixing device in said bore adapted to have ingredients pass through said valve and then through said device to be mixed, the other member of said unit slidably receiving at least a portion of said one member and at one end being connected to one end of an operating member adapted to be moved toward and from said one member, and a valve member on said operating member at least coextensive in area and aligned with one end of said static mixing device and adapted to abut said one end of said device and close it against passage of material therethrough when moved toward said one member and when movement of said operating member is reversed said valve member is moved away from said end of said device and opens the adjacent end of said static mixing device for passage of material therethrough to be mixed.

12. The flow control valve according to claim 11 further including movement limiting means interconnected between said longetudinally movable members and comprising a groove or slot of predetermined length in one of said members and at least one projecting member fixed to the other member and slidable within said groove or slot.

13. A mixing syringe for a plurality of different flowable materials comprising in combination, a hollow-body having a discharge end, and a plurality of side by side compartments respectively to contain said different materials, a piston-like member movable longitudinally in said body and having at least one passage therethrough, at least one valve member adapted to close said passage in said piston-like member when the same is adjacent the discharge end of body and thereby prevent escape of material from said compartments until mixing thereof is desired, and an actuating member which is elongated and flat and extends between opposite side walls of said hollow body to form said compartments, and wherein said piston-like member comprises a pair of first and second longitudinally movable members having means to restrict the amount of relative movement therebetween, and said elongated actuating member being connected to the first member which is nearest the end of the actuating member on which the valve member is mounted and the second member of the piston-like member having said longitudinal passage therethrough and slidably extending through said first member, and in which said activating member opens said valve member opening said passage and mixing said different materials and then moving said piston-like member away from the discharge end of said body toward the other end thereof and thereby forcing the materials in said compartments to interengage and mix.

14. The mixing syringe according to claim 13 in which said second member has an elongated diametrically reduced portion on one end and said first member has a bore slidably receiving said reduced portion of said second member for the full length thereof, and movement-limiting means on said members comprising a slot in one member and a pin or screw on the other slidably received in said slot.

* * * * *